United States Patent [19]

Murakami et al.

[11] 4,051,126

[45] Sept. 27, 1977

[54] PROCESS FOR THE PREPARATION OF 6-ALKOXY-SUBSTITUTED PENICILLINS

[75] Inventors: Masuo Murakami, Tokyo; Ichiro Isaka, Hoys; Teruya Kashiwagi, Ageo, all of Japan

[73] Assignee: Yamanouchi Pharmaceutical Co., Ltd., Tokyo, Japan

[21] Appl. No.: 704,770

[22] Filed: July 13, 1976

Related U.S. Application Data

[63] Continuation of Ser. No. 533,124, Dec. 16, 1974, abandoned.

[30] Foreign Application Priority Data

Dec. 26, 1973  Japan ................................. 48-3259
Nov. 12, 1974  Japan ............................... 49-130145

[51] Int. Cl.² .................. C07D 499/44; C07D 499/58
[52] U.S. Cl. .................................................. 260/239.1
[58] Field of Search ...................................... 260/239.1

[56] References Cited

U.S. PATENT DOCUMENTS

| 3,778,432 | 12/1973 | Pines ................................. 260/239.1 |
| 3,843,641 | 10/1974 | Christensen et al. ............. 260/239.1 |
| 3,994,885 | 11/1976 | Koppel ............................. 260/243 C |

OTHER PUBLICATIONS

J.A.C.S. 94, 1408-1411 (1972).
J.A.C.S. 95, 2403 (1973).
J.A.C.S. 95, 2401 (1973).
Weygond, "Preparative Organic Chemistry".

*Primary Examiner*—Gerald A. Schwartz
*Attorney, Agent, or Firm*—Burgess, Ryan and Wayne

[57] ABSTRACT

An improved process of preparing a 6-alkoxy-substituted penicillin or penicillin sulfoxide is disclosed. This process comprises adding a halogenating agent to penicillin or penicillin sulfoxide while cooling, and then adding an alkali metal alcoholate to the hydrogenation product in the presence of an alcohol corresponding to the alcoholate.

14 Claims, No Drawings

PROCESS FOR THE PREPARATION OF 6-ALKOXY-SUBSTITUTED PENICILLINS

This is a continuation, of application Ser. No. 533,124, filed Dec. 16, 1974, now abandoned.

DETAILED DESCRIPTION OF THE INVENTION

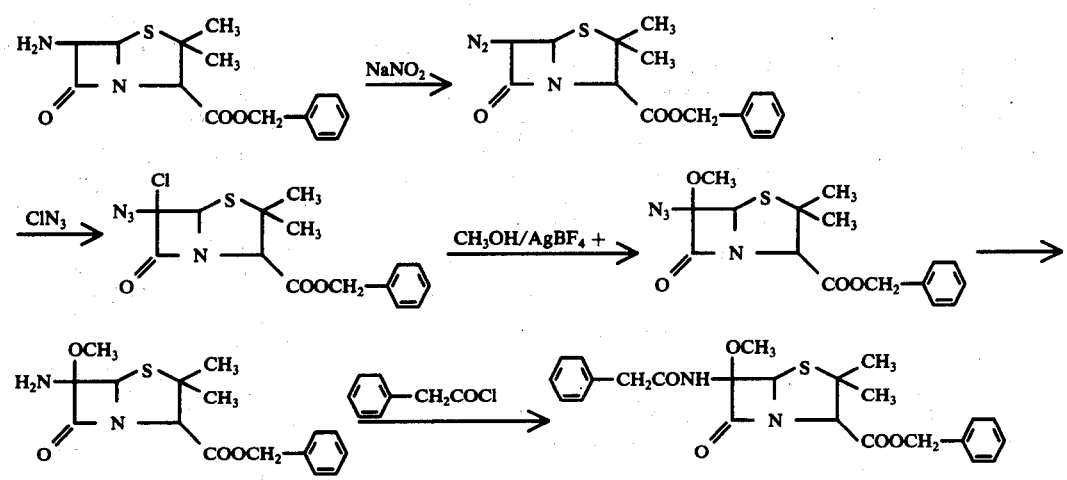

The present invention relates to an improved process for introducing a substituted hydroxy group in the 6-position of a penicillin derivative. More particularly it relates to a novel process of preparing a 6-substituted penicillin derivative represented by the general formula III

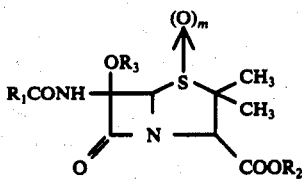

III wherein $R_1CO$ represents an organic acyl group;

$R_2$ represents an ester residue;

$R_3$ represents an alkyl group, an alkenyl group, an alkynyl group, a cycloalkyl group, or an aralkyl group; and $m$ is 1 or 0 by adding a halogenated agent to an inert organic solvent solution of a penicillin derivative represented by general formula I

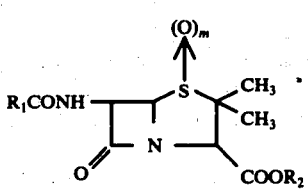

I wherein $R_1$, $R_2$, and $m$ have the same meaning as in general formula III.

While cooling and then adding to the product an alkali metal alcoholate represented by general formula II

MOR$_3$  II wherein $R_3$ has the same meaning as in general formula III and M represents an alkali metal in the presence of the alcohol corresponding to the alcoholate.

In the process for introducing a substituent to the 6-position of a penicillin compound, a series of reactions shown by, for example, the following scheme have hitherto been disclosed:

(See, for example, Journal of the American Chemical Society; 94, 1408–1411(1972)). However, since the process has a large number of steps and gives a low yield of the final product. This process is unsuitable for industrial use.

An improved process having less steps, is known. This process comprises adding an alkali metal alcoholate such as lithium methoxide, etc., or an aryl alkali metal such as phenyl lithium, etc., to an inert organic solvent solution of penicillin at a very low temperature, i.e., $-80°$ C., to form the alkali metal salt. A halogenating agent such as t-butyl hypochlorite, etc., is added to the salt in the presence of an alcohol (See, for example, Journal of the American Chemical Society. 95, 2403(1973) and Journal of Organic Chemistry, 38, 1436(1973)).

Although the production steps may be reduced in such an improved process the carbon-sulfur bond of the penicillin skeleton is broken even at a very low temperature of $-80°$ C. to form a considerable amount of by-products, which results in lowering the yield for the final product. Further, the reaction product must be purified by means of column chromatography, etc., for removing these by-products.

On the other hand, there is also known a process in which penicillin sulfoxide is reacted with a halogenating agent such as t-butyl hypochloride, etc., in methanol containing a buffer solution of sodium borate at 0° C. (See, for example Journal of the American Chemical Society, 95, 2401(1973)).

In this process the carbon-sulfur bond of the penicillin skeleton is difficult to break even at 0° C. owing to the use of penicillin sulfoxide as the starting material and hence the formation of by-products is less. However the yield of the final product is still low, i.e., about which makes this process uneconomical for industrial practice.

As a result of various investigations, the inventors have discovered that the 6-substituted pencillin derivative shown by formula III can be unexpectedly obtained at a high yield by adding first a halogenating agent to an inert organic solent solution of a penicillin derivative of formula I accomplished by cooling and adding an alkali metal alcoholate of the formula II in the presence of the corresponding alcohol (R₃OH) and further, since in this process the carbon-sulfur bond of the penicillin skeleton is difficult to break even if the reaction is carried out at temperature of form 0° to −30° C./and no by-product is formed, a purification step such as column chromatography for the product is unnecessary.

Since, according to the process of this invention, a halogenating agent is added at first and then the alkali metal alcoholate of formula II is added in the presence of the corresponding alcohol, the alkali metal salt of the starting material of formula I which is formed immediately reacts with the halogenating agent and further, the halogenated product is then reacted with the corresponding alcohol, this results in preventing the formation of by-products and providing the desired 6-substituted penicillin derivative of the formula III in a high yield.

As the compound of formula I, which is the starting material of this invention, there are many known penicillin compounds.

The starting material of this invention will be explained more in detail. In the compound shown by general formula I, R₁CO is a stable organic acyl group which does not contribute to the reaction and suitable examples of the organic acyl group in which acyl is a residue of a carboxylic acid are a phenylacetyl group, a phenylpropionyl group, a 2-phenylbutylyl group, a formul group, an acetyl group, a propionyl group, a butylyl group, a phenoxyacetly group, a penoxypropionyl group, a phenoxybutylyl group, a benzoyl group, a nitrobenzoyl group, a methylbenzoyl group, a dimethylbenzoyl group, a methoxybenzoyl group, a 2,6-dimethoxybenzoyl group, an ethoxybenzoyl group, a diethoxybenzoyl group, and α-azidophenylacetyl group, a methoxynaphthoyl group, a 2-ethoxy-α-naphthoyl group, a furylbutylyl group, a furylacetyl group, a thiencylacetyl group, a thienylpropionyl group, an octanoyl group, a 5-methyl-3-phenyl-4-isoxazolylcarbonyl group, a 3-(2-chlorophenyl)-5-methyl-4-isoxazolylcarbonyl group, a 3-(2,6-dichlorophenyl)-5-methyl-4-isoxazolylcarbonyl group, an 60 -aminophenylacetyl, an α-aminothienylacetyl group, a 1-aminocyclohexylacarbonyl group, an α-amino-1,4-cyclohexadienylacetyl group, and an α-amino-p-hydroxyphenylacetyl group.

R₂ is an ester residue and suitable examples of such an ester residue are a methyl group, a butyl group, a 2,2,2-trichloroethyl group, a phenacyl group, a methoxylbenzyl group, a nitrobenzyl group, a benzhydryl group, a bis(p-methoxyphenyl)methyl group, trityl group, a trimethylsilyl group, a fluorenyl group, a p-bromophenacyl group, a phthalimidomethyl group, a benzyl group, a p-nitrobenzyl group, a p-methoxybenzyl group, a p-toluenesulfonylmethyl group, a trimethyltin group, a β-(methylsulfonyl)ethyl group, a β-dimethylaminoethyl group, a phthalidyl group, a diphenylmethyl group, a benzoylmethyl group, a p-bromobenzoylmethyl group, an acyloxybenzyl group substituted by a lower alkyl group such as a propionyloxybenzyl group, or a p-pivaloyloxybenzyl group an acyloxybenzyl group substituted by a lower alkyl group such as, a 3,5-dimethyl-4-acetyloxybenzyl group or, a 3,5-di-tert-butyl-4-acetyloxybenzyl group, a dichlorobenzhydryl group such as a 2,4'-dichlorobenzyhydryl group, or a 4,4'-dichlorobenzyhydryl group, a 2,4,4'-trichlorobenzhydryl group, and a tetrachloro-9,10-dihydro-9-anthryl group such as a 1,5,10,10-tetrachloro-9.10-dihydro-9-anthryl group.

Also, R₃ is an alkyl group, an alkenyl group, an alkynyl group, a cycloalkyl group, or an aralkyl group. Suitable examples of an alkyl group are a methyl group, an ethyl group, an isopropyl group, a butyl group, an isobutyl group, etc.; suitable examples of an alkenyl group are an allyl group, a butenyl group, etc.; suitable examples of an alkynyl group are propargyl group, etc.; suitable examples of a cycloalkyl group are a cyclohexyl group, a cyclopentyl group, etc.; and suitable examples of the aralkyl group are a benzyl group, a phenethyl group, etc.

In a typical practice of the process of this invention, a slightly excessive amount of more than 1.3 equivalent of the halogenating agent is added to an inert organic solvent solution of the pencillin derivative of formula I accompanied by cooling to, usually, at temperatures of 0° C. to −30° C. and then about 1 equivalent of the alkali metal alcoholate of formula II is added to the product in the presence of the corresponding alcohol (R₃OH) in, usually, an excessive amount.

Examples of an inert organic solvent are methylene chloride, dichloroethane, tetrahydrofuran etc., and examples of a halogenating agent are a hypochloride or M-haloimide compound etc., such as t-butyl hypochloride N-chloroacetamide, N-chlorosuccinimide, N-bromosuccinic acid imide, N-bromophthalimide, etc.

The 6-substituted penicillin derivative of formula III, in which m is 1, thus obtained can be converted into a penicillin derivative having excellent antibacterial activity by releasing the ester after reduction of the sulfoxide or the aforesaid compound is further converted into a cephalosporin derivative having excellent antibacterial activity by releasing the ester after ring expansion.

Furthermore, the 6-substituted penicillin derivative of formula III, in which m is 0, is converted into a pencillin derivative having excellent antibacterial activity by converting the acyl group into another acyl group or can be further converted into a cephalosporin derivative having excellent antibacterial activity by oxidizing to form a sulfoxide and then expanding the ring and then removing the ester.

The following Examples illustrate the process of the present invention and are not to be considered as limiting the invention.

EXAMPLE 1 a. In 36 ml. of methylene chloride was dissolved 3.64 g. of benzylpenicillin sulfoxide methyl ester and after adding further to the solution 1.63 g. of tert-butyl hypochlorite having a purity of about 90%, the mixture was cooled to −25° C. Then, a solution was prepared by dissolving 0.85 g. of lithium methoxide having a purity of about 50% in 8.5 ml. of methanol was added dropwise to the mixture at temperatures of from −20° C. to −25° C. in a nitrogen gas stream over a period of about 1 hour and the resultant mixture was stirred for 1 hour at the same temperature. After adding 0.7 ml. of acetic acid, the reaction mixture was washed, in succession, with cold water, a cooled aqueous 5% sodium hydrogen carbonate solution, a cooled aqueous 5% sodium thiosulfate solution, and cold water and dried over anhydrous sodium sulfate. Then, by subjecting the product to evaporation to dryness under a reduced pressure, 3.9 g. (99%) of a light-yellow powder of 6α-methoxybenzylpenicillin sulfoxide methyl ester was obtained.

Elemental analysis for $C_{18}H_{22}N_2O_6S$:

|  | C(%) | H(%) | N(%) | S(%) |
|---|---|---|---|---|
| Calculated: | 54.81 | 5.62 | 7.10 | 8.13 |
| Found: | 54.27 | 5.44 | 6.63 | 8.19 |

Infrared absorption spectra:
$\nu_{max}^{KBr}$ cm$^{-1}$: 1785, 1750, 1680.

Nuclear magnetic resonance spectra (in CDCl$_3$): p δ: 1.16 (3H, s), 1.60 (3H, s), 3.32 (3H, s), 3.58 (1H, d, J=3H$_z$), 3,64 (1H, d, J=3H$_z$), 3.75 (3H, s), 4,67 (1H, s), 5.04 (1H, s), 7.27 (5H, s), and 7.81 (1H, s).

b. In 11 ml. of dimethyl formamide was dissolved 2.65 g. of 6α-methoxybenzylpenicillin sulfoxide methyl ester and the solution was cooled to −8° C. Then, a solution of 2.73 g. of phosphorus tribromide in 3 ml of benzene was added dropwise to the solution at temperatures of from −3° C. to −8° C. over a period of 12 minutes and the mixture was stirred for 30 minutes at the same temperature. Then, 30 ml. of ethyl acetate was added in layer, the reaction mixture was dispersed in a cooled aqueous 5% sodium hydrogen carbonate solution, and the ethyl acetate layer formed was separated from the aqueous layer. The aqueous layer was extracted with 10 ml. of ethyl acetate and the extract was combined with the ethyl acetate layer. The mixture was washed with water and dried over anhydrous magnesium sulfate. After concentrating the product under a reduced pressure to 5 ml., 30 ml. of petroleum ether was added, whereby a glutinous meterial formed. The glutinous material was recovered by decantation and dried in vacuo to give 2.26 g. of the yellow powder of 6α-methoxybenzylpenicillin methyl ester.

Infrared absorption spectra:
$\nu_{max}^{KBr}$ cm$^{-1}$: 1780, 1745, 1665.

Nuclear magnetic resonance spectra (in CDCl$_3$):
δ: 1.39 (6H, s), 3.40 (3H, s), 3.63 (2H, s), 3.75 (3H, s), 4.37 (1H, s), 5.57 (1H, s), and 7.30 (5H, s).

EXAMPLE 2 a. In 48 ml. of methylene chloride was dissolved 4.85 g. of benzylpenicillin sulfoxide p-nitrobenzyl ester and after adding further to the solution 1.63 g. of tert-butyl hypochlorite having a purity of about 90%, the mixture was cooled to −20° C. Then, a solution of 0.85 g. of lithum methoxide oxide having a purity of about 50% in 8.5 ml. of methanol was added dropwise to the mixture at the same temperature in a nitrogen gas stream over a period of about 1 hour and the resultant mixture was stirred for 40 minutes at the same temperature. After adding 0.6 ml. of acetic acid, the reaction mixture was washed, in succession, with cold water, a cooled aqueous 5% sodium hydrogen carbonate solution, a cooled aqueous 5% sodium thiosulfate solution, and cold water and then was dried over anhydrous magnesium sulfate.

By subjecting the product to evaporation to dryness under a reduced pressure, 4.8 g. (93.3%) of the light-yellow powder of 6α-methoxybenzylpenicillin sulfoxide p-nitrobenzyl ester was obtained.

Elemental analysis for $C_{24}H_{25}N_3O_8S$:

|  | C(%) | H(%) | N(%) | S(%) |
|---|---|---|---|---|
| Calculated: | 55.92 | 4.89 | 8.15 | 6.22 |
| Found: | 55.49 | 4.92 | 7.85 | 6.10 |

Nuclear magnetic resonance spectra (in CDCl$_3$):

δ: 1.15 (3H, s), 1.61 (3H, s), 3.34 (3H, s), 3.63 (2H, s), 4.75 (1H, s), 5.04 (1H, s), 5.32 (2H, s), 7.28 (5H, s), 7.53 (2H, d, J=9Hz), 8.19 (2H, d, J=9Hz), and 7.60 (1H, s).

Infrared absorption spectra:
$\nu_{max}^{KBr}$ cm$^{-1}$: 1785, 1750, and 1675.

b. In 5 ml. of dimethylformamide was dissolved 1.1 g. of 6α-methoxybenzylpenicillin sulfoxide p-nitrobenzyl ester and the solution was cooled to −15° C. Then, a solution of 0.81 g. of phosphorus tribromide in 1 ml. of ethyl acetate was added dropwise to the mixture over a period of 4 minutes and the resultant mixture was stirred for 35 minutes at 0° C. Then, 30 ml. of ethyl acetate was added in a layer, the reaction mixture was dispersed in a cooled aqueous 5% sodium hydrogen carbonate solution, and after stirring the dispersion for 5 minutes under ice cooling, the aqueous layer that formed was separated from the ethyl acetate layer. The aqueous layer was extracted with 15 ml. of ethyl acetate and the extract was combined with the ethyl acetate layer. The mixture was washed, in succession, with a cooled aqueous sodium hydrogen carbonate solution and ice water and then dried over anhydrous magnesium sulfate. After concentrating the product under a reduced pressure to 5 ml., 30 ml. of petroleum ether was added to the concentrate, whereby an oily material formed. When the oily material was mixed with 10 ml. of ether and the mixture was allowed to stand for 30 minutes, the oily material was solidified. The solid product was recovered by decantation and dried over phosphorus pentoxide under a reduced pressure to give 0.95 g. (89.2%) of a yellowish powder of 6α-methoxybenzylpenicillin p-nitrobenzyl ester.

Infrared absorption spectra:
$\nu_{max}^{KBr}$ cm$^{-1}$: 1775, 1745, 1675.

Nuclear magnetic resonance spectral (in CDCl$_3$):
δ: 1.36 (6H, s), 3.39 (3H, s), 3.63 (2H, s), 4.45 (1H, s), 5.27 (2H, s), 5.56 (1H, s), 7.18 (1H, s), 7.18 (1H, s), 7.30 (5H, s), 7.53 (2H, d, J=8Hz), and 8.20 (2H, d, J=8Hz)

c. In 50 ml. of dioxane were dissolved 2.3 g. of 6α-methoxybenzylpenicillin sulfoxide p-nitrobenzyl ester and 59.2 mg. of phenylphosphoric acid 24.4 mg. of pyridine and the solution was refluxed for 17 hours. The reflux was carried out while drying the liquified dioxane with a molecular sieve. The solvent was distilled off from the reaction mixture under a reduced pressure and the residue obtained was dissolved in 50 ml. of ethyl acetate. The solution was washed with an aqueous 5% sodium hydrogen carbonate solution and water and then dried over anhydrous magnesium sulfate. Then, by subjecting the product to evaporation to dryness, 1.8 g. of a brown powder was obtained. The powder was applied to a silica gel column chromatography and purified using a mixture of benzene and ethyl acetate of 4 : 1 by volume ratio to give 7α-methoxy-7β-phenylacetamidodesacetoxycephalosporanic acid p-nitrobenzyl ester having a melting point of 131°–132° C.

Elemental analysis for $C_{24}H_{23}N_3O_7S$:

|  | C(%) | H(%) | N(%) | S(%) |
|---|---|---|---|---|
| Calculated: | 57.94 | 4.66 | 8.45 | 6.44 |
| Found: | 57.98 | 4.73 | 8.43 | 6.46 |

Infrared absorption spectra:
$\nu_{max}^{KBr}$ cm$^{-1}$: 1780, 1720, and 1680.

Nuclear magnetic resonance spectra (in D$_6$-DMDO):

δ: 2.06 (3H, s), 3.38 (5H, s), 3.63 (2H, s), 5.12 (1H, s), 5.40 (2H, s), 7.29 (5H. s), 7.68 (2H, d, J=9Hz), 8.22 (2H, d, J=9Hz), and 9.44 (1H, s).

EXAMPLE 3 a. In 150 ml. of methylene chloride was dissolved 9.36 g. of benzylpenicillin sulfoxide phenacyl ester and after adding to the solution 3.3 g. of tert-butylhypochlorite having a purity of about 90%, the mixture was cooled to −25° C. Then, a solution of 1.7 g. of lithium methoxide having a purity of about 50% in 17 ml. of methanol was added dropwise to the mixture at temperatures of from −25° C. to −20° C. in a nitrogen gas stream over a period of 70 minutes and the resultant mixture was stirred for 20 minutes at the same temperature. After adding 1 ml. of acetic acid to the reaction mixture, a product was treated as in Example 1 to give 9.5 g. (96.0%) of a light-yellow powder of 6α-methoxybenzylpenicillin sulfoxide phenacyl ester.

Infrared absorption spectra:
$\nu_{max}^{KBr}$ cm$^{-1}$: 1784, 1760, and 1685.

Nuclear magnetic resonance spectra (in CDCl$_3$):
δ: 1.45 (3H, s), 1.75 (3H, s), 3.36 (3H, s), 3.67 (2H, s), 4.75 (1H, s), 5.03 (1H, s), 5.22 (1H, d, J=16Hz), 5.68 (1H, d, J=16 Hz), 7.00 (1H, s), 7.29-7.33 (5H, m), {7.51 (1H, d, J=8Hz)} × 2, 7.57 (1H, s), {7.89 (1H, d, J=8, 2Hz} × 2.

Elemental analysis for (C$_{25}$H$_{26}$N$_2$O$_7$S):

|  | C(%) | H(%) | N(%) | S(%) |
| --- | --- | --- | --- | --- |
| Calculated: | 60.23 | 5.26 | 5.62 | 6.43 |
| Found: | 59.86 | 5.24 | 5.21 | 6.17 | b-1. In 14 ml. of dimethylformamide was dissolved 2.8 g. of 6α-methoxybenzylpenicillin sulfoxide phenacyl ester and the solution was cooled to −15° C. Then, a solution of 2.3 g. of phosphorus tribromide in 3 ml. of ethyl acetate was added dropwise to the solution over a period of 10 minutes and the mixture was stirred for 30 minutes at 0° C. Thereafter, 70 ml. of ethyl acetate was added in a layer, the reaction mixture was dispersed in a cooled aqueous 5% sodium hydrogen carbonate solution and then the aqueous layer was separated from the ethyl acetate layer. The aqueous layer was extracted with 20 ml. of ethyl acetate and the extract was combined with the ethyl acetate layer. The mixture was washed with a cooled aqueous 5% sodium hydrogen carbonate solution and then ice water and dried over anhydrous magnesium sulfate. Then, after concentrating to 10 ml. under a reduced pressure, 50 ml. of petroleum ether was added to the concentrate, whereby a solid formed. After allowing the system to stand for 1 hour at 0° C., the solid was recovered by decantation and dried over phosphorus pentoxide under a reduced pressure to give 2.3 g. (85%) of the yellowish powder of 6α-methoxybenzylpenicillin phenacyl ester.

Infrared absorption spectra:
$\nu_{max}^{KBr}$ cm$^{-1}$: 1780, 1760, and 1690.

Nuclear magnetic resonance spectra (in CDCl$_3$):
δ: 1.47 (3H, s), 1.59 (3H, s), 3.40 (3H, s), 3.65 (2H, s), 4.51 (1H, s), 5.41 (2H, s), 5.60 (1H, s), 7.02 (1H, s), 7.32 (5H, s), {7.50 (1H, d, J=8Hz)} × 2, 7.57 (1H, s), {(7.91 (1H, d, J=8, 2Hz)} × 2.

Elemental analysis for C$_{25}$H$_{26}$N$_2$O$_6$S:

|  | C(%) | H(%) | N(%) | S(%) |
| --- | --- | --- | --- | --- |
| Calculated: | 62.23 | 5.43 | 5.81 | 6.64 |
| Found: | 61.92 | 5.54 | 5.42 | 6.50 | b-2. In 1 ml. of dimethylformamide was dissolved 0.97 g. of 6α-methoxybenzylpenicillin phenacyl ester and after adding to the solution 0.27 g. of sodium thiphenolate, the mixture was stirred for 30 minutes. Then, 30 ml. of ether was added gradually to the reaction mixture, whereby a solid formed. The solid was recovered by decantation and dissolved in 10 ml. of ice water. The solution was washed with ethyl acetate. Then, 15 ml. of ethyl acetate was added in a layer, the pH of the aqueous layer formed was adjusted to about 2 by diluted hydrochloric acid and the ethyl acetate layer formed was separated from the aqueous layer. The aqueous layer was extracted with ethyl acetate and the extract was combined with the ethyl acetate layer. The mixture was washed with water and dried over anhydrous magnesium sulfate. Then, the mixture was concentrated to 3 ml. under a reduced pressure, after adding 1 ml. of n-butanol solution of 20% sodium n-ethylhexanoate, 30 ml. of ether was added gradually to the mixture with stirring, and the resultant mixture was further stirred for 10 minutes, whereby crystals formed. The crystals were recovered by filtration, washed with ether, and dried over phosphorus pentoxide in vacuo to give 0.63 g. of 6-methoxydibenzylpenicillin sodium having a melting point of 146°-146° C.

Elemental analysis for C$_{17}$H$_{21}$N$_2$O$_6$SNa:

|  | C(%) | H(%) | N(%) | S(%) |
| --- | --- | --- | --- | --- |
| Calculated: | 50.49 | 5.23 | 6.93 | 7.93 |
| Found: | 51.03 | 5.03 | 6.89 | 7.54 |

Infrared absorption spectra:
$\nu_{max}^{KBr}$ cm$^{-1}$: 1765 and 1670.

Nuclear magnetic resonance spectra (in CD$_3$OD).
δ: 1.43 (3H, s), 1.48 (3H, s), 3.43 (3H, s), 3.61 (2H, s), 4.19 (1H, s), 5.53 (1H, s), 7.29 (5H, s).

c. A mixture of 1.1 g of 6α-methoxybenzylpenicillin sulfoxide phenacyl ester, 29.6 mg. of phenylphosphoric acid, 12.2 mg. of pyridine, and 10 ml. of dioxane was refluxed for 8 hours. The reflux was carried out while drying the liquefied dioxane with a molecular sieve. The solvent was distilled off from the reaction mixture and the residue was dissolved in ethyl acetate. The solution was washed with an aqueous 5% sodium hydrogen carbonate solution and then water and dried over anhydrous magnesium sulfate. The product was concentrated under a reduced pressure and n-hexane was added to the concentrate, whereby a solid formed. The solid was recovered by decantation and dried to give 10 g. of a brown powder. The powder was dissolved in methylene chloride, applied to a silica gel column chromatography, and purified using a mixture of benzene and ethyl acetate of 4 : 1 by volume ratio as an eluate to give 7α-methyloxy-7β-phenylacetamidodesacetoxycephalosporanic acid phenacyl ester having a melting point of 199°-202° C.

Elemental analysis for C$_{25}$H$_{24}$N$_2$O$_6$S:

|  | C(%) | H(%) | N(%) | S(%) |
| --- | --- | --- | --- | --- |
| Calculated: | 62.49 | 5.03 | 5.83 | 6.67 |

-continued

Elemental analysis for $C_{25}H_{24}N_2O_6S$:

|  | C(%) | H(%) | N(%) | S(%) |
|---|---|---|---|---|
| Found: | 61.97 | 4.91 | 5.42 | 6.94 |

Infrared absorption spectra:
$\nu_{max}^{KBr}$ cm$^{-1}$: 1765, 1737, 1700, and 1665.

Nuclear magnetic resonance spectra (in $D_6$-DMSO):
δ: 2.11 (3H, s), 3.22 (3H, d, J=18Hz), 3.35 (3H, s), 3.61 (1H, d, J=18Hz), 3.61 (2H, s), 5.12 (1H, s), 5.69 (2H, t), 7.28 (5H, s), {7.59 (1H, d, J=8Hz)} × 2, 7.63 (1H, s), 8.02 (1H, d, J=8, 2Hz), 9.41 (1H, s).

EXAMPLE 4

In 25 ml. of methylene chloride was dissolved 2.58 g. of benzylpenicillin sulfoxide benzhydryl ester and after adding to the solution 0.82 g. of tert-butylhypochlorite having a purity of about 90%, the mixture was cooled to −30° C. Then, a solution of 0.43 g. of lithium methoxide having a purity of about 50% in 4 ml. of methanol was added dropwise to the mixture at temperatures of from −20° C. to −30° C. in a nitrogen gas stream over a period of 1 hour and then the resultant mixture was stirred for 1 hour at the same temperature. The reaction mixture was mixed with 0.3 ml. of acetic acid, the mixture was washed, in succession, with cold water, a cooled aqueous 5% sodium hydrogen carbonate solution, a cooled aqueous 5% sodium thiosulfate solution, and cold water and dried over anhydrous sodium sulfate. Then, by subjecting the product to evaporation to dryness under a reduced pressure, 2.6 g. of a light-yellow powder of 6α-methoxybenzylpenicillin sulfoxide benzhydryl ester was obtained.

Infrared absorption spectra:
$\nu_{max}^{KBr}$ cm$^{-1}$: 1785, 1745 and 1685

Nuclear magnetic resonance spectra (in CDCl$_3$):
δ: 0.90 (3H, s), 1.59 (3H, s), 3.34 (3H, s), 3.61 (2H, s), 4.72 (1H, s), 4.95 (1H, s), 6.96 (1H, s), and 7.28 (15H, m).

Elemental analysis for $C_{30}H_{30}N_2O_6S$:

|  | C(%) | H(%) | N(%) | S(%) |
|---|---|---|---|---|
| Calculated: | 65.92 | 5.53 | 5.12 | 5.85 |
| Found: | 65.53 | 5.74 | 5.39 | 5.41 |

EXAMPLE 5

In 49 ml. of methylene chloride was dissolved 4.84 g. of 6-phenoxyacetamidopenicillanic acid sulfoxide phenacyl ester and after adding 1.45 g. of tert-butyl hypochlorite having a purity of about 90% to the solution, the mixture was cooled to −30° C. Then, 8 ml. of a methanol solution containing 0.4 g. of lithium methoxide havin a purity of about 100% was added dropwise to the mixture at temperatures of from −20° C. to 31 30° C. in a nitrogen gas stream over a period of 1 hour and then the resultant mixture ws stirred for 15 minutes at the same temperature. The reaction mixture was mixed with 0.2 ml. of ethyl acetate and the mixture was treated as in Example 1 to give 4.8 g. of a light-yellow powder of 6α-methoxy-6β-phenoxyacetamidopenicillanic acid sulfoxide phenacyl ester.

Infrared absorption spectra:
$\nu_{max}^{KBr}$ cm$^{-1}$: 1795, 1765, and 1700.

Nuclear magnetic resonance spectra (in CDCl$_3$):
δ: 1.45 (3H, s), 1.73 (3H, s), 3.44 (3H, s), 4.55 (2H, d, J=2Hz), 4.73 (1H, s), 5.07 (1H, s), 5.24 (1H, d, J=16Hz), 5.65 (1H, d, J=16 Hz), and 6.89–7.93 (9H, m).

EXAMPLE 6

In 45 ml. of methylene chloride was dissolved 3.16 g. of 6-p-nitrobenzoylamidopenicillanic acid sulfoxide methyl ester and after adding to the solution 1.2 g. of tert-butyl hypochlorite having a purity of 90%, the mixture was cooled to −30° C. Then, 6 ml. of a methanol solution containing 0.33 g. of lithium methoxide having a purity of about 100% was added dropwise to the mixture at temperatures of from 31 30° C. to −35° C. in a nitrogen gas stream over a period of 1 hour and then the resultant mixture was stirred for 5 minutes at the same temperature. The reaction mixture was mixed with 0.1 ml. of acetic acid and the mixture was treated as in Example 1 to give 3.13 g. of a light-yellow powder of 6α-methoxy-6β-p-nitrobenzoylamidopenicillanic acid sulfoxide methyl ester.

Infrared absorption spectra:
$\nu_{max}^{KBr}$ cm$^{-1}$: 1790, 1755 (shoulder), and 1675.

Nuclear magnetic resonance spectra:
δ: 1.23 (3H, s), 1.60 (3H, s), 3.54 (3H, s), 3.81 (3H, s), 4.63 (1H, s), 5.10 (1H, s), 7.99 (2H, d, J=8Hz), 8.19 (2H, d, J=8 Hz), and 8.29 (1H, s).

EXAMPLE 7

In 35 ml. of methylene chloride was dissolved 3.5 g. of benzylpenicillin methyl ester and after adding to the solution 1.63 g. of tert-butyl hypochlorite having a purity of about 90%, the mixture was cooled to −30° C. Then, a solution of 0.4 g. of lithium methoxide having a purity of about 100% in 6 ml. of methanol was added dropwise to the mixture at temperatures of from −25° C. to −30° C. in a nitrogen gas stream over a period of 1 hour and then the resultant mixture was stirred for 10 minutes at the same temperature. The reaction mixture was mixed with 0.1 ml. of acetic acid and the mixture was washed, in succession, with cold water, a cooled aqueous 5% sodium hydrogen carbonate solution, a cooled aqueous 5% sodium thiosulfate solution, and cold water and dried over anhydrous sodium sulfate. The, by subjecting the mixture to evaporation to dryness under a reduced pressure, 3.43 g. of a light-yellow powder of 6α-methoxy-6β-benzylpenicillin methyl ester was obtained.

Infrared absorption spectra:
$\nu_{max}^{KBr}$ cm$^{-1}$: 1780, 1745, and 1665.

Nuclear magnetic resonance spectra (in CDCl$_3$):
δ: 1.38 (3H, s), 3.39 (3H, s), 3.74 (3H, s), 4.38 (1H, s), 5.58 (1H, s), 7.30 (5H, s), and 7.54 (1H, s).

These results coincided well with the infrared absorption spectra and the nuclear magnetic resonance spectra of the 6α-methoxy-6β-benzylpenicillin methyl ester obtained by reducing 6α-methoxy-6β-benzylpenicillin sulfoxide methyl ester.

EXAMPLE 8

In 47 ml. of methylene chloride was dissolved 4.68 g. of 6-phenoxyacetamidopenicillanic acid phenacyl ester and after adding to the solution 1.7 g. of tert-butyl hypochlorite having a purity of about 90%, the mixture was cooled to −30° C. Then, a methanol solution containing 0.42 g. of lithium methoxide having a purity of about 100% was added dropwise to the mixture at temperatures of from −25° C. to −30° C. in a nitrogen gas stream over a period of 1 hour. The resultant mixture was stirred for 5 minutes at the same temperature. The reaction mixture was mixed with 0.1 ml. of acetic acid and the mixture was treated as in Example 1 to give 4.62 g. of a light-yellow powder of 6α-methoxy-6β-phenoxyacetamidopenicillanic acid phenacyl ester.

Infrared absorption spectra:
$\nu_{max}^{KBr}$ cm$^{-1}$: 1780, 1755, and 1695.

Nuclear magnetic resonance spectra (in CDCl$_3$):
δ: 1.51 (3H, s), 1.61 (3H, s), 3.48 (3H, s), 4.52 (1H, s), 4.54 (2H, s), 5.38 (1H, d, J=2Hz), 5.44 (1H, d, J=2Hz), 5.63 (1H, s), and 6.88-7.92 (10H, m).

What is claimed is:

1. A process of preparing a 6-substituted penicillin compound of the formula:

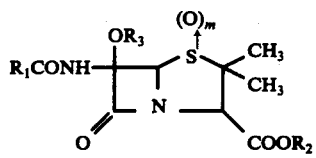

wherein R$_1$CO is phenyl lower alkanoyl, phenoxy lower alkanoyl, benzoyl, or benzoyl substituted by nitro, lower alkyl or lower alkoxy in the benzene ring; R$_2$ is lower alkyl, lower alkyl substituted by phenyl, nitrophenyl, halo-phenyl or lower alkoxy phenyl; benzoyl, or benzoyl substituted by nitro, halo, or lower alkoxy; R$_3$ is lower alkyl; and m is 1 or 0 which consists essentially of the steps of (a) first adding a halogenating agent to an inert organic solvent solution of a penicillin compound of the formula:

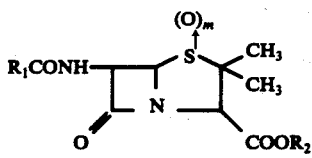

where R$_1$, R$_2$ and m have the same meaning as defined above, under cooling at a temperature of about 0° C. to about −30° C. and then (b) adding to the reaction mixture about one equivalent of an alkali metal alcoholate of the formula

MOR$_3$ wherein R$_3$ has the same meaning as in the above formula and M represents an alkali metal in the presence of an alcohol corresponding to said alcoholate.

2. A process according to claim 1 in which about 1.3 equivalents of said halogenating agent is added to said inert organic solvent solution of said penicillin compound.

3. A process according to claim 1 in which said inert organic solvent is a member selected from the group consisting of methylene chloride, dichloroethane and tetrahydrofuran.

4. A process according to claim 1 in which said halogenating agent is a member selected from the group consisting of t-butylhypochlorite, N-chloroacetamide, N-chloro succinimide, N-bromosuccinimide, and N-bromophthalimide.

5. A process according to claim 1 in which said alkali metal alcoholate is lithium methoxide and the corresponding alcohol is methanol.

6. A process according to claim 1 in which said 6-substituted penicillin compound is 6α-methoxybenzyl penicillin sulfoxide methyl ester and said penicillin compound is benzyl-penicillin sulfoxide methyl ester.

7. A process according to claim 7 in which said 6-substituted penicillin compound us 6α-methoxybenzyl penicillin sulfoxide p-nitrobenzyl ester and said penicillin compound is benzyl penicillin sulfoxide p-nitrobenzyl ester.

8. A process according to claim 1 wherein said 6-substituted penicillin compound is 6α-methoxybenzyl penicillin sulfoxide phenacyl ester and said penicillin compound is benzylpenicillin sulfoxide phenacyl ester.

9. A process according to claim 1 in which said 6-substituted penicillin compound is 6α-methoxybenzyl penicillin sulfoxide benzhydryl ester and said penicillin compound is benzylpenicillin sulfoxide benzhydryl ester.

10. A process according to claim 1 in which said 6-substituted penicillin compound is 6α-methoxy-6β-phenoxyacetamido-penicillanic acid sulfoxide phenacyl ester and said penicillin compound is 6-phenoxyacetamidipenicillanic acid sulfoxide phenacyl ester.

11. A process according to claim 1 in which said 6-substituted penicillin compound is 6α-methoxy-6β-p-nitrobenzoylamidopenicillanic acid sulfoxide methyl ester and said penicillin compound is 6-p-nitrobenzoylamidopenicillanic acid sulfoxide methyl ester.

12. A process according to claim 1 in which said 6-substituted penicillin compound is 6α-methoxy-6β-benzyl penicillin methyl ester and said penicillin compound is benzyl penicillin methyl ester.

13. A process according to claim 1 in which said 6-substituted penicillin compound is 6α-methoxy-6β-phenoxyacetamidopenicillanic acid phenacyl ester and said penicillin compound is 6-phenoxyacetamidopenicillanic acid phenacyl ester.

14. A process according to claim 1 in which about one equivalent of said alkali metal alcoholate is added to said reaction mixture in the presence of an excess amount of the alcohol corresponding to said alkali metal alcoholate.

* * * * *

UNITED STATES PATENT OFFICE
CERTIFICATE OF CORRECTION

Patent No. 4,051,126  Dated September 27, 1977

Inventor(s) Masuo Murakami, et al

It is certified that error appears in the above-identified patent and that said Letters Patent are hereby corrected as shown below:

In the Title Page, under "Inventors", lines 2 & 3: "Hoys" should be --Tokyo--; "Ageo" should be --Saitama--.

in the Abstract, line 5: "hydrogenation" should be --halogenated--.

Column 1, line 50: "halogenated" should be --halogenating--.

line 63: Delete the period.

line 64: "While" should be --while--.

Column 2, line 5: Change "to" to --in--.

line 32: "product. This" should be --product, this-- line 34: Delete the comma.

UNITED STATES PATENT OFFICE
CERTIFICATE OF CORRECTION

Patent No. 4,051,126           Dated September 27, 1977

Inventor(s) Masuo Murakami, et al

It is certified that error appears in the above-identified patent and that said Letters Patent are hereby corrected as shown below:

Column 2, line 46:   After "process" insert a comma.

line 55:   "hypochloride" should be --hypochlorite--.

line 56:   Insert a comma after "borate".

line 63:   After "about" insert --60%,--.

Column 3, line 2:   "accomplished" should be --accompanied--; after "formula I" insert a comma.

line 3:   After "formula II" insert a comma.

line 7:   "form" should be --from--; "C./" should be --C.--.

line 31:   "formul" should be --formyl--.

line 32:   "phenoxyacetly" should be --phenoxyacetyl--.

line 37:   "and" should be --an--.

line 40:   "thiencylacetyl" should be --thienylacetyl--.

line 44:   "60 -" should be -- $\alpha$ - --.

UNITED STATES PATENT OFFICE
CERTIFICATE OF CORRECTION

Patent No. 4,051,126             Dated September 27, 1977

Inventor(s)         Masuo Murakami, et al

It is certified that error appears in the above-identified patent and that said Letters Patent are hereby corrected as shown below:

Column 3, line 45: "aminocyclohexylacar-" should be --aminocyclohexylcar- --.

line 50: "methoxylben-" should be --methoxyben- --.

line 61: "propionyloxybenzyl" should be -- p-propionyloxybenzyl --.

line 62: After "group" insert a comma.

line 63: After "as" delete the comma.

lines 66 & 67: "dichlorobenzyhydryl" should be --dichlorobenzhydryl--.

Column 4, line 1: "9.10" should be --9, 10--.

line 12: "the" should be --an--.

line 25: "hypochloride" should be --hypohalite--.

line 26: "M" should be --N--.

line 27: "ride" should be --rite,--.

line 28: "bromosuccinic acid imide" should be --bromosuccinimide--.

UNITED STATES PATENT OFFICE
CERTIFICATE OF CORRECTION

Patent No. 4,051,126  Dated September 27, 1977

Inventor(s) Masuo Murakami, et al

It is certified that error appears in the above-identified patent and that said Letters Patent are hereby corrected as shown below:

Column 5, line 10: " p δ:" should be --δ:--.

line 31: "meterial" should be --material--.

line 33: "2.26" should be --2.28--.

line 47: "lithum methoxide oxide" should be --lithium methoxide--.

Column 6, line 38: "7.18(1H,s)," (2nd occurrence) should be deleted.

line 42: After "acid" insert a comma.

last line: "DMDO" should be --DMSO--.

Column 7, line 29: "2Hz}" should be --2Hz)}--.

Column 8, line 10: "thipheno-" should be --thiopheno- --.

line 32: "146°-146°C." should be --146°-148°C.--.

line 48: "liquefied" should be --liquified--.

line 61: "methyloxy" should be --methoxy--.

Column 9, line 55: "havin" should be --having--.

UNITED STATES PATENT OFFICE
CERTIFICATE OF CORRECTION

Patent No. 4,051,126                    Dated September 27, 1977

Inventor(s)        Masuo Murakami, et al

It is certified that error appears in the above-identified patent and that said Letters Patent are hereby corrected as shown below:

Column 9, line 56:  "31 30°" should be -- -30° --.

Column 10, line 12:  "31 30°C." should be -- -30°C. --.

Column 12, line 10:  "N-chloro succinimide" should be --N-chlorosuccinimide--.

line 19:  "claim 7" should be --claim 1--.

line 20:  "us" should be --is--.

line 36:  "acetamidipenicillanic" should be --acetamidopenicillanic--.

Signed and Sealed this

Second Day of May 1978

[SEAL]

Attest:

RUTH C. MASON
Attesting Officer

LUTRELLE F. PARKER
Acting Commissioner of Patents and Trademarks